United States Patent [19]

Sturm

[11] Patent Number: 5,084,062
[45] Date of Patent: Jan. 28, 1992

[54] DEVICE FOR STOPPING THE FLOW OF BLOOD IN EXTREMITIES

[76] Inventor: Martina E. Sturm, Nicolai-Hartmann-Str. 138, D- 5090 Leverkusen, Fed. Rep. of Germany

[21] Appl. No.: 499,295
[22] PCT Filed: Nov. 14, 1988
[86] PCT No.: PCT/DE88/00710
§ 371 Date: May 17, 1990
§ 102(e) Date: May 17, 1990
[87] PCT Pub. No.: WO89/04637
PCT Pub. Date: Jun. 1, 1989

[30] Foreign Application Priority Data

Nov. 17, 1987 [DE] Fed. Rep. of Germany ....... 3738903

[51] Int. Cl.[5] .............................................. A61B 17/12
[52] U.S. Cl. ....................................... 606/203; 24/168
[58] Field of Search .................. 606/203; 24/168, 169, 24/576

[56] References Cited

U.S. PATENT DOCUMENTS

| | | | |
|---|---|---|---|
| 2,604,098 | 7/1952 | Kranc | 606/203 |
| 3,349,449 | 10/1967 | Hatfield | 24/197 |
| 4,398,324 | 8/1983 | Bakker et al. | 24/615 X |
| 4,640,281 | 2/1987 | Sturm et al. | 24/115 M X |

FOREIGN PATENT DOCUMENTS

| | | |
|---|---|---|
| 3538583 | 6/1986 | Fed. Rep. of Germany . |
| 3602778 | 8/1987 | Fed. Rep. of Germany ...... 606/203 |
| 2501484 | 9/1982 | France . |

OTHER PUBLICATIONS

International Search Report, 2/28/89.
International Preliminary Examination Report, 1/24/90.

Primary Examiner—Michael H. Thaler
Attorney, Agent, or Firm—Eckert Seamans Cherin & Mellott

[57] ABSTRACT

A device for ligaturing parts of the body comprises a flat strap (15) of elastic material in the form of a loop (35) and a buckle attached to the latter comprising a clamping part (1) and a releasing part (2). The clamping part comprises a basic element (29) which forms a basic supporting and guiding surface (39) in the longitudinal direction of the strap (15) and has lateral faces between which the strap passes and which have locking elements ensuring a releasable connection between the clamping part (1) and the releasing part (2). The latter is connected to one end (22) of the strap, has locking elements which releasably connect it to the clamping part (1) and a clamping region (3) at the end opposite the loop (35) whose distance from the surface (39) is located in the region of the thickness of the released strap (15) when the strap buckle is assembled. When the strap buckle is assembled, the locking elements form a pivoting joint. When pressure is exerted on a front external face (18) of the releasing part (2) located between the locking elements and the buckle (35), the clamping part (3) moves away from the basic surface (39), thereby releasing the device. On the end of the clamping part (1) facing the buckle (35), a transverse rib (12) projects from the basic surface (39) towards the releasing part (2), by a distance equal to the thickness, preferably twice the thickness, of the strap. As it passes over the transverse rib, the strap (15) changes direction.

12 Claims, 2 Drawing Sheets

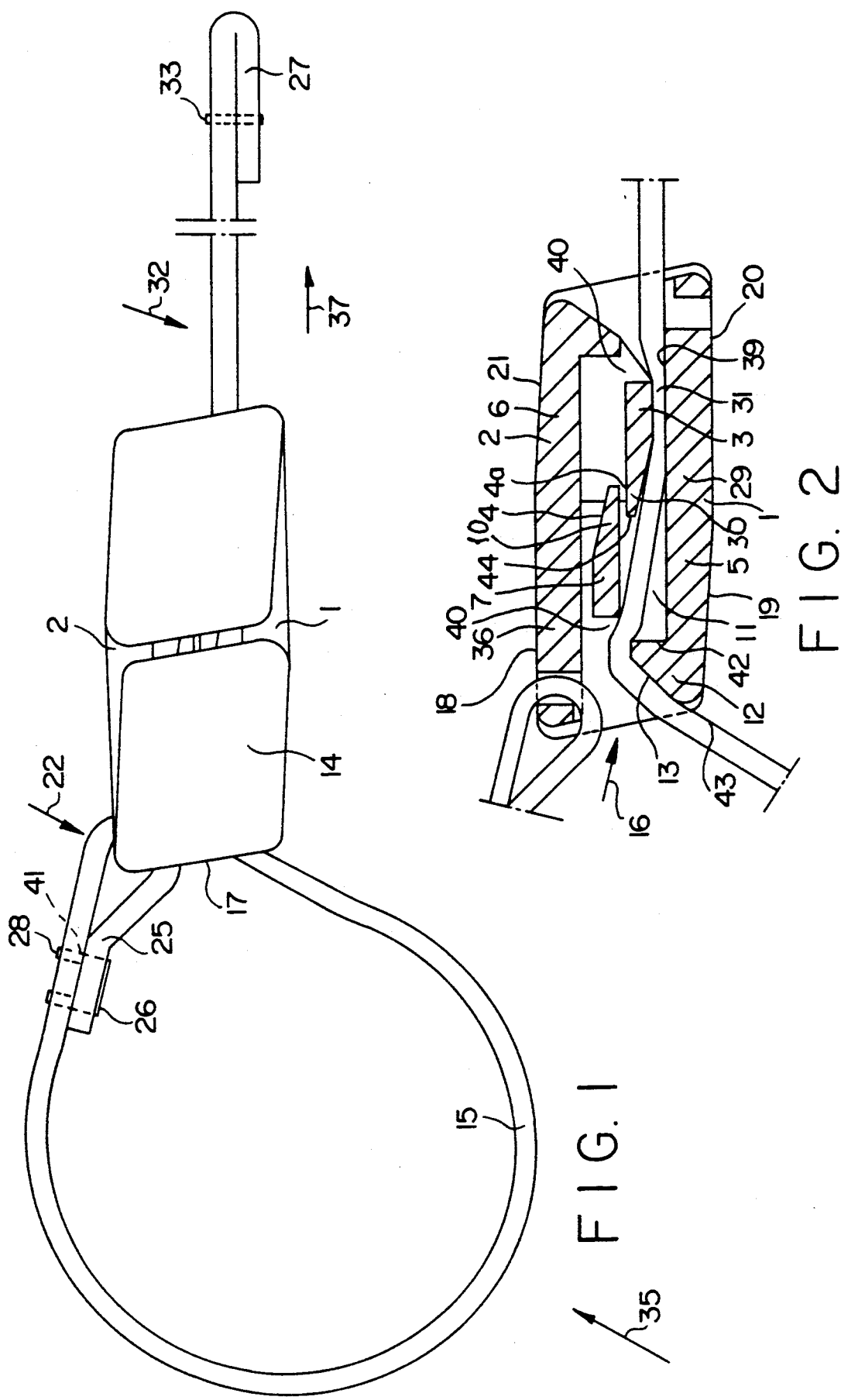

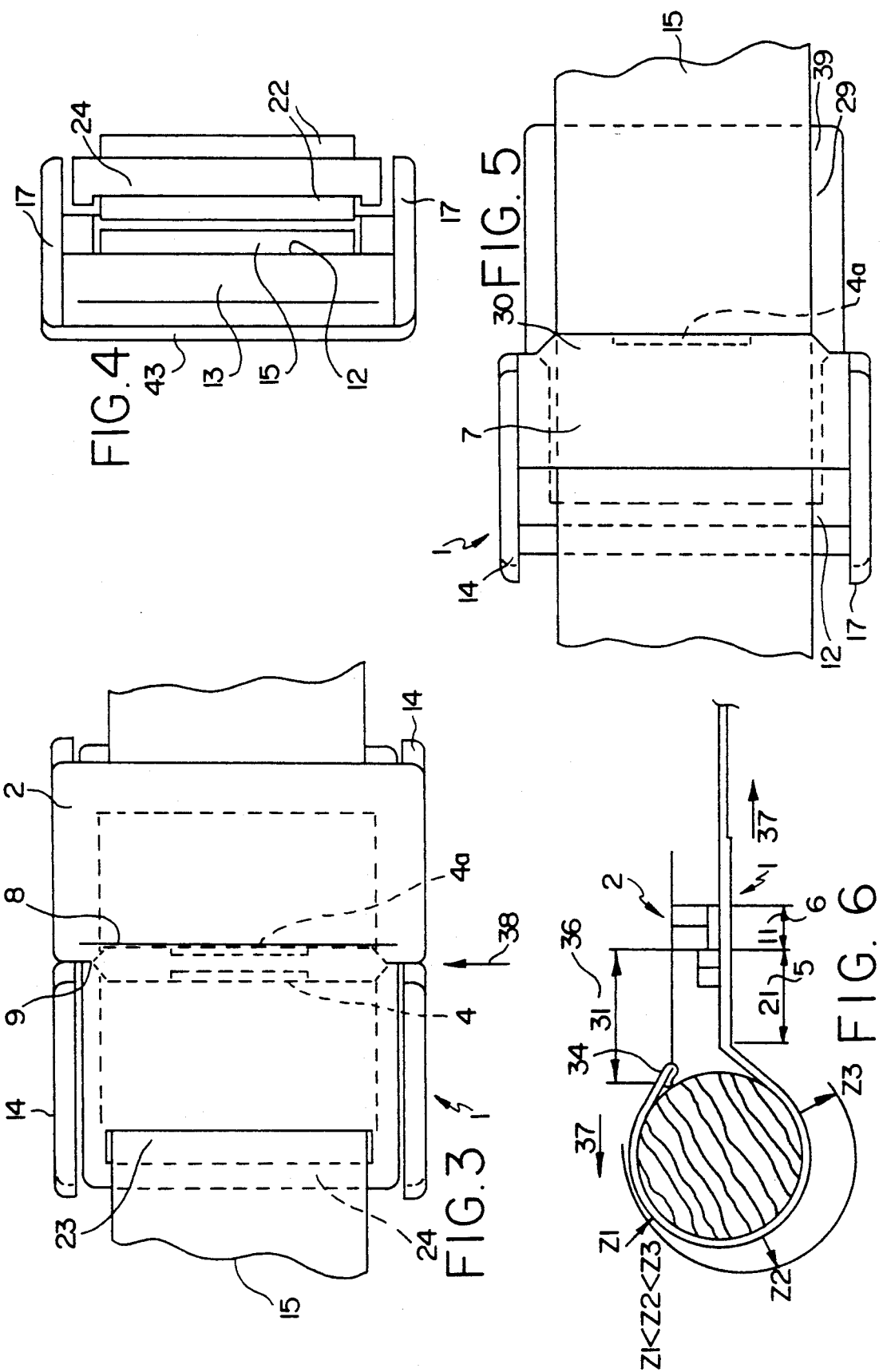

DEVICE FOR STOPPING THE FLOW OF BLOOD IN EXTREMITIES

The invention pertains to a device for stopping the flow of blood in extremities as described in the characterizing part of claim 1.

In this device, which is already known from DE-OS 35 38 583, the base runs flat as far as the forward edge of the clamping device, i.e., the edge facing the loop. The part of the strap that forms the loop is bent at the forwardmost edge of the base, forcing the strap to follow a path along the base. The strap is clamped farther back on the base in the clamping zone.

When the device is used, the loop is placed around an extremity, for example, an arm, and the end of the strap is pulled through the clamping device until the loop surrounds the arm tightly enough. When this is done, the loop becomes smaller, a segment of the strap is pulled into the clamping device over the above-described forward edge, and the end of the strap extending beyond the clamping device becomes longer. However, when the loop is tightened and the strap enters the clamping device, the skin in contact with the inner surface of the strap is pulled along with the loop and forms a fold. As the loop is drawn further into the strap clamp, the fold of skin is clamped tighter and tighter, causing pain.

The objective of the invention was to improve the device of the type described above in such a way that skin cannot be drawn into the strap clamp so far as to cause pain.

This objective is accomplished by the device specified in patent claim 1.

The transverse rib initially raises the strap higher than is necessary for the strap to run into the base. It then runs down to the base and, at least in the clamping region, rests against the base. Therefore, the strap is bent at a greater angle than in state-of-the art devices of this type. As a result, the skin that is drawn in by friction is behind the transverse rib and thus no longer rests against the strap inside the strap clamping device. The transverse rib produces separation between the strap and the skin that is drawn in frictionally by the strap. This could also be described as a type of separation edge. This eliminates tight squeezing of the skin and prevents pain. The skin is still drawn in by the strap, but it is no longer pulled into a constriction transverse to the strap, where pinching or clamping could occur.

In another design, the transverse rib has an inclined surface for supporting the strap. The inclined surface basically follows the direction of the entering segment of the loop. In this way, the bending of the strap does not occur directly at the front face but rather a few millimeters behind it, e.g., three to five millimeters.

In another design improvement, the inclined surface is inclined at an angle of 30° to 60° to the base and preferably at an angle of 45°. This produces the desired, relatively large bending angle of the strap. The inclined surface defines the angle of entry of the strap; behind the inclined surface and the transverse rib, the strap is bent back towards the base in the opposite direction. In this way, there is a total bend of at least 50° (with respect to the unbent direction).

In another design improvement, the upper edge of the transverse rib is displaced relative to a frontal face of the clamping device that faces the loop, and it is preferably displaced by at least the width of the strap. This also causes the strap to bend inside the strap clamping device.

Additional advantages and features of the invention are described in the other claims and in the following description of a specific example of the invention with reference to the attached drawings. It is understood that this example merely serves to illustrate the invention and in no way limits it.

FIG. 1 shows a full view of a specific embodiment of the invention.

FIG. 2 is a cross section of the device shown in FIG. 1.

FIG. 3 represents a top view of the device.

FIG. 4 is a front view with the strap cut.

FIG. 5 shows a top view corresponding to FIG. 3, except that only the clamping part 1 is shown, i.e., with the release device 2 removed.

FIG. 6 shows an action diagram of the lever and the force distribution in a representation corresponding to FIG. 1.

The drawings in FIGS. 1 to 5 show the device in its tightened working position.

The device consists of a strap 15 that forms a loop 35 with a portion of its total length, the clamping part 1 and the release part 2. Clamping part 1 and release part 2 are geometrically equal parts (congruent parts) and can be fastened together by lengthwise movement (in the longitudinal direction of the strap 15) and released in the opposite direction. A bridge-like structure is mounted on a basically rectangular foundation 29. This bridge-like structure consists of two congruent side walls 14 and a bridge part 7 connecting them. The latter part has a beveled, roof-like projecting part 10. In the extended state of the strap 15, i.e., with the loop 35 released, the release part 2 is located at one end of the strap, and the clamping part 1 is located along the length of the strap. In this position of the device, the two parts 1 and 2 are displaced with respect to each other in the longitudinal direction of the strap 15. To form the loop 35 starting from this position, one part is moved 180° around an axis lying transverse to the plane of the strap, leading to the arrangement of parts 1 and 2 that is shown in FIG. 1 to 4 and FIG. 6, in which the roof-like projection 30 the release part 2 hooks under the roof-like projection 10 of clamping part 1, acting as locking mechanisms, locking clamping part 1 and release part 2 together and at the same time a pivot joint is formed at this point.

If there is no tension in the loop 35, i.e., if the strap clamping device is not in its tightened working position, the clear opening 31 of the clamping zone 3 is just large enough to allow the strap 15 to be moved in the longitudinal direction. However, as shown in FIGS. 2 and 6, as soon as a tensile stress exists in the loop 35 and as a result the front ends of the two parts 1 and 2 that face the loop 35 are moved away from each other, the tightened working position shown in the drawings is attained. This reduces the clear opening 31, causing the strap 15 to be clamped in clamping zone 3. The strap 15 passes through a chamber 11 in the clamping part 1. The thickness of the loose end of the strap 32 is increased by folding over and clamping (clamp 33) the strap material (overlapping 27) to prevent the strap from being pulled out inadvertently.

The strap's other end 22, which is permanently attached to the release part 2, is undetachably connected by wrapping it around crossbar 24 and clamping the overlapped portion 25 of the strap with a longitudinally placed clamp 26. The strap material is both longitudinally and transversely elastic.

The loop 35 formed by strap 15 is placed around the extremity to be compressed. The release part 2 is hooked together with the clamping part 1 by moving it longitudinally. The strap 15 is tightened by pulling the free end 32 of the strap. This presses the clamping part 1 against the strap in the clamping zone 3. The resulting strap tension Z increases along the circumference of loop 35 from the permanent attachment loop 34 at the release part 2 towards the clamping part 1 (Z1, Z2, Z3), so that the strap 15 is secured by clamping in clamping zone 3 with the long lever arm 5 of the clamping part 1 and the common fulcrum 4 to prevent its movement in the longitudinal direction.

Compression of the limb is also achieved in the strap entry region of the device by the projecting surfaces 17.

The strap tensile force "Z" decreases along the circumference of the limb, so that only residual tensile force "Z1" opposes the release of release part 2.

When outer surface 18 of release part 2 is lifted, the release lever length 36 exerts a large leverage on the forward release part 2 in the downward direction towards the clamping part 1 to terminate the clamping effect in clamping zone 3 and allows gentle release of the compression. The process of gentle release of compression is enhanced by a deflection of the strap on a transverse rib 12 at the front face and by the resulting strap friction.

After the strap tensile force is removed, by lightly pulling the roof-like projection 10 of the release part 2 back from the chamber 11 of the clamping part 1, the release part 2 is easily separated.

In the released state of the device, the surface 18 of the release part 2 and the surface 19 of the clamping part 1 form a wedge inclined towards the strap loop 35 to make it easier to manipulate the device during removal of compression, release and separation. The increased thickness 27 of the strap material in clamping zone 3 in the released state of the device pushes the parts into the advantageous position described above.

A transverse rib 12 extending the entire width of the strap and running at right angles to the strap is located at the forward end of the foundation 29. The transverse rib 12 can be designed in any desired way. In the specific example shown in the drawings, the transverse rib 12 is a one-piece component of the clamping part 1, which itself otherwise consists of a single piece. However, it can also be an inserted, possibly rotatable axis, a number of projections arranged side by side transverse to the strap direction, or a similar design. The only critical feature is that the strap must pass over an edge, which in the example shown in the drawings is the highest elevation of the transverse rib 12. The upper, inner side of the foundation forms a base 39 that extends practically the entire length of the foundation. The transverse rib 12 projects several milimeters, for example, 2 to 3 milimeters, from this base 39. Expressed in slightly different terms, it projects from the base 39 at least the thickness of the strap and in a preferred design of the invention at least twice the thickness of the strap (i.e., 4 to 6 mm). Towards the front surface 17 the transverse rib 12 is bounded by an inclined surface 13 which is inclined at an angle of 45° to the base 39. The upper edge of the transverse rib is thus not in the immediate vicinity of the front surface (which should not be expressly excluded), but rather is displaced inwardly (by about 5 mm in the example shown in the drawings). The inclined surface 13 becomes a rounded edge 43 towards the forward outer surface 19 of the clamping part 1. This rounded edge is located slightly (only a few tenths of a millimeter) behind the front face 17. On the side of the strap 15 turned away from the clamping part 1, a free space towards the release part 2 or towards the end 22 of the strap is left between the front surface 17 and the upper edge of the transverse rib 12. This free space is wider than the single width of the strap. Specifically, it does not taper like a funnel, but rather widens out behind the upper edge and as far as the beginning of the bridgelike structure 7 of the clamping part 1, so that skin cannot be pulled in in a funnel-like fashion in this area.

Between the transverse rib 12 and the bridge part 7 of the clamping part 1 there is a slot for the passage of the strap. Behind this slot the strap passes through a chamber 11 and comes to a position below the clamping zone 3, where it is clamped. This is the first point at which the strap comes into contact with the base 39.

An edge of the bridge part, which extends over the entire width of the strap, rests against the surface of the strap that forms the inner surface of the loop. As FIG. 2 shows, this edge is positioned in such a way with respect to the transverse rib 12 that the strap is bent very slightly in the opposite direction from the direction in which the strap is bent by the transverse rib. This gives the strap a slightly S-shaped course. However, the bend at the edge of the bridge part 7 is much smaller, for example, less than 10°, while the bend at the transverse rib is at least five times and preferably ten times greater.

I claim:

1. A device for stopping a flow of blood in extremities, comprising:

a flat strap made of an elastic material that forms a loop, and a strap-clamping device attached to the strap and having a clamping part and a release part;

the clamping part having a foundation that forms a base for supporting and guiding the strap in a longitudinal direction, and side walls, the clamping part having a first locking mechanism for releasably fastening the clamping part and the release part, the strap passing between the clamping part and the release part;

the release part being attached to one end of the strap, and having a second locking mechanism for releasably fastening the clamping part, defining a clamping zone at a far end of the release part away from the loop;

a distance between the clamping zone and the base in an assembled state of the strap locking device being approximately equal to a thickness of the strap when loose, whereby a clamping action is achieved between the base and the clamping zone;

in the assembled state of the strap-clamping device, on one hand, the first and second locking mechanisms connecting the clamping part with the release part, and on the other hand, the first and second locking mechanisms forming a pivot joint;

the release part having an outer surface, which is located between the first and second locking mechanisms and the loop, and when a forward part of this outer surface is pressed, the clamping zone becoming separated from the base, thereby releasing the clamping action;

a transverse rib projecting from the base at a loop end of the clamping part by a distance at least equal to the thickness of the strap so that the strap runs down to the base after passing the transverse rib, the transverse rib forming an inclined surface for supporting the strap and the inclination of the inclined surface corresponding basically to a direction of the entering part of the loop that rests upon it.

2. The device in accordance with claim 1, wherein the inclined surface is inclined to the base at an angle of 30° to 60°.

3. The device in accordance with claim 1, wherein the inclined surface is inclined to the base at an angle of about 45°.

4. A device for stopping a flow of blood in extremities, comprising:

a flat strap made of an elastic material that forms a loop, and a strap-clamping device attached to the strap and having a clamping part and a release part;

the clamping part having a foundation that forms a base for supporting and guiding the strap in a longitudinal direction, and side walls, the clamping part having a first locking mechanism for releasably fastening the clamping part and the release part, the strap passing between the clamping part and the release part;

the release part being attached to one end of the strap, and having a second locking mechanism for releasably fastening the clamping part, defining a clamping zone at a far end of the release part away from the loop;

a distance between the clamping zone and the base in an assembled state of the strap locking device being approximately equal to a thickness of the strap when loose, whereby a clamping action is achieved between the base and the clamping zone;

in the assembled state of the strap-clamping device, on one hand, the first and second locking mechanisms connecting the clamping part with the release part, and on the other hand, the first and second locking mechanisms forming a pivot joint;

the release part having an outer surface, which is located between the first and second locking mechanisms and the loop, and when a forward part of this outer surface is pressed, the clamping zone becoming separated from the base, thereby releasing the clamping action;

a transverse rib projecting from the base at a loop end of the clamping part by a distance at least equal to the thickness of the strap so that the strap runs down to the base after passing the transverse rib, an upper edge of the transverse rib being inwardly displaced with respect to a front face of the clamping part facing the loop and being separated from the front face by at least the width of the strap.

5. The device in accordance with claim 4, wherein the strap is bent at the transverse rib by at least 50°.

6. The device in accordance with claim 5, wherein the clamping part has a bridge part connecting the side walls, an opening being defined between the bridge part and the transverse rib for passage of the strap, the strap being in contact with an edge of the bridge part, and the direction of the strap being changed by a small angle at this edge, such that this bend in the strap is in an opposite direction from the bend produced at the transverse rib.

7. The device in accordance with claim 6, wherein the small angle of bend at the edge is less than 10° in the opposite direction from the bend produced at the transverse rib.

8. The device in accordance with claim 4, wherein the release part has a slot for holding a retaining loop of the strap.

9. The device in accordance with claim 4, wherein a free space is defined between the front face and the transverse rib on the side of the strap facing the clamping part, this free space being at least as great as the thickness of the strap.

10. The device in accordance with claim 9, wherein the free space between the front face and the transverse rib on the side of the strap facing the clamping part is greater than 2 mm.

11. The device in accordance with claim 4, wherein the upper edge of the transverse rib is inwardly displaced with respect to a front face of the clamping part facing the loop and is separated from the front face by 4 to 6 mm.

12. The device in accordance with claim 4, wherein the strap is bent at the transverse rib by at least 60°.

* * * * *